United States Patent [19]

Mosesson et al.

[11] Patent Number: 5,985,833
[45] Date of Patent: Nov. 16, 1999

[54] THROMBIN INHIBITOR

[75] Inventors: Michael W. Mosesson, Shorewood; David A. Meh, Milwaukee, both of Wis.

[73] Assignee: Wisconsin Alumni Research Foundation, Madison, Wis.

[21] Appl. No.: 08/713,885

[22] Filed: Sep. 17, 1996

[51] Int. Cl.$^6$ .............................. A61K 38/03; C07K 7/08
[52] U.S. Cl. .............................. 514/13; 514/14; 530/326; 530/327; 530/382
[58] Field of Search .................................... 514/2, 14, 13, 514/12; 530/324, 326, 327, 382

[56] References Cited

U.S. PATENT DOCUMENTS

| | | | |
|---|---|---|---|
| 5,182,260 | 1/1993 | Maraganore et al. | 514/12 |
| 5,196,403 | 3/1993 | Maraganore et al. | 514/12 |
| 5,196,404 | 3/1993 | Maraganore et al. | 514/13 |
| 5,240,913 | 8/1993 | Maraganore et al. | 514/13 |
| 5,242,810 | 9/1993 | Maraganore et al. | 435/69.2 |
| 5,256,559 | 10/1993 | Maraganore et al. | 435/240.2 |
| 5,425,936 | 6/1995 | Maraganore et al. | 424/1.69 |
| 5,433,940 | 7/1995 | Maraganore et al. | 424/1.69 |
| 5,446,131 | 8/1995 | Maraganore | 530/326 |

OTHER PUBLICATIONS

Hortin et al. Inhibition of Thrombin's Clotting Activity by Synthetic Peptide Segements of its Inhibitors and Substrates, Biochemical and Biophysical Research Communications, vol. 169, No. 2, pp. 437–442. Jun. 15, 1990.

Maraganore et al. Design and Characterization of Hirulogs: A Novel Class of Bivalent Peptie Inhibitors of Thrombin, Biochemistry vol. 29, pp. 7095–7101, 1990.

Hortin et al. 'Allosteric Changes in Thrombin's Activity Produced by Peptides Corresponding to Segments of Natrual Inhibitors and Substrates', Journal of Biological Chemistry, vol. 266 pp. 6866–687, Apr. 1991.

L.J. Berliner and Y. Sugawara, "Human α–Thrombin Binding to Nonpolymerized Fibrin–Sepharose: Evidence for an Anionic Binding Region," Biochemistry 24:7005–7009, 1985.

E. Kaczmarek and J. McDonagh, "Thrombin Binding to the Aα–, Bβ–, and γ–Chains of Fibrinogen and to Their Remnants Contained in Fragment E," 263 (27) :13896–13900, 1988.

J.M. Maraganore, et al., "Anticoagulant Activity of Synthetic Hirudin Peptides," J. Biol. Chem. 264 (15) 8692–8698, 1989.

D.A. Meh, et al., "Identification and Characterization of the Thrombin Binding Sites on Fibrin," J. Biol. Chem. 271 (38) :23121–23125, 1996.

M.A.A. Parry, et al., "Kinetic Mechanism for the Interaction of Hirulog with Thrombin," Biochemistry 33:14807–14814, 1994.

M. Guillin, et al., "Thrombin Specificity," Thrombosis and Haemostasis 74(1):129–133, 1995.

N.E. Kirschbaum, et al., "Characterization of the γ Chain Platelet Binding Site on Fibrinogen Fragment D," Blood 79(10):2643–2648, 1992.

D.H. Farrell, et al., "Recombinant Human Fibrinogen and Sulfation of the γ' Chain," Biochemistry 30:9414–9420, 1991.

K.R. Siebenlist and M.W. Mosesson, "Peak 2 fibrinogen serves as the carrier of plasma factor XIII," Abstract 48, Blood Coagulation and Fibrinolysis 4:833, 1993.

S.O. Lawrence, et al., "Purification and Functional Characterization of Homodimeric γB–γB Fibrinogen From Rat Plasma," Blood 82(8):2406–2413, 1993.

C.G. Binnie and S.T. Lord, "The Fibrinogen Sequences That Interact With Thrombin," Blood 81(12:3186–3192, 1993.

J.M. Maraganore, et al., "Design and Characterization of Hirulogs: A Novel Class of Bivalent Peptide Inhibitors of Thrombin," Biochemistry 29:7095–7101, 1990.

G.L. Hortin, "Sulfation of a Gamma–Chain Variant of Human Fibrinogen," Biochemistry International 19(6):1355–1362, 1989.

D.L. Amrani, et al., "The Role of Fibrinogen Aα Chains in ADP–Induced Platelet Aggregation in the Presence of Fibrinogen Molecules Containing γ' Chains," Blood 72(3):919–924, 1988.

C.W. Francis, et al., "Carboxyl–terminal amino acid sequences of two variant forms of the γ chain of human plasma fibrinogen," Proc. Natl. Acad. Sci. USA 85:3358–3362, 1988.

D.W. Ghung and E.W. Davie, "γ and γ' Chains of Human Fibrinogen Are Produced By Alternative mRNA Processing," Biochemistry 23:4232–4236, 1984.

G.A. Homandberg, et al., "Amino Acid Sequences of the Carboxyl–Terminal Regions of Rat Plasma Fibrinogen $\gamma_A$ and γ' Chains," Thrombosis Research, 39:263–269, 1985.

M.W. Mosesson, et al., "Human Platelet Fibrinogen Gamma Chain Structure," Blood 63(5):990–995, 1984.

C.D. Legrele, et al., "Evidence For Two Classes Of Rat Plasma Fibrinogen γ Chains Differing By Their Cooh–Terminal Amino Acid Sequences," Biochemical and Biophysical Research Communications 105(2):521–520, 1982.

C. Wolfenstein–Todel and M.W. Mosesson, "Carboxy–Terminal Amino Acid Sequence of a Human Fibrinogen γ–Chain Variant (γ')," Biochemistry 20:6146–6149, 1981.

C. Wolfenstein–Todel and M.W. Mosesson, "Human plasma fibrinogen heterogeneity: Evidence for an extended carboxyl–terminal sequence in a normal γ chain variant (γ')," Proc. Natl. Acad. Sci. USA 77(9):5069–5073, 1980.

(List continued on next page.)

Primary Examiner—Cecilia J. Tsang
Assistant Examiner—Anish Gupta
Attorney, Agent, or Firm—Quarles & Brady LLP

[57] ABSTRACT

A thrombin inhibitor is disclosed. The thrombin inhibitor comprises: (1) a segment which inactivates or sequesters thrombin; (2) a segment comprising a portion of the fibrinogen γ' chain that binds to the thrombin exosite, such as amino acid residues (414–427) and amino acid residues (414–425) of the native human fibrinogen γ' sequence.

2 Claims, 8 Drawing Sheets

OTHER PUBLICATIONS

C.Y. Liu, et al., "The Binding of Thrombin by Fibrin*," *The Journal of Biological Chemistry* 254(20):10421–10425, 1979.

N.E. Stathakis, et al., "Human Fibrinogen Heterogeneities. Preparation and Characterization of γ and γ' Chains*," *Thrombosis Research* 13:467–475, 1978.

M.W. Mosesson, et al., "Human Fibrinogen Heterogeneities," *The Journal of Biological Chemistry* 247(16):5223–5227, 1972.

G.L. Hortin and B.M. Benutto, "Inhibition of Thrombin's Clotting Activity By Synthetic Peptide Segments Of Its Inhibitors And Substrates," *Biochemical and Biophysical Research Communications* 169(2):437–442, 1990.

THROMBIN INHIBITOR

This invention was made with United States government support awarded by NIH, grant #NIH Award #HL47000. The United States Government has certain rights in this invention.

FIELD OF THE INVENTION

In general, the field of the present invention is thrombin inhibitors. Specifically, the field of the present invention is a thrombin inhibitor comprising amino acid sequences found in the human fibrinogen gamma prime (γ') sequence.

BACKGROUND

Thrombin binds to its substrate fibrinogen in the central amino-terminal region and cleaves fibrinopeptides A and B from the Aα and Bβ chains, respectively, converting fibrinogen to fibrin. The thrombin-fibrinogen binding interaction is mediated through an anion-binding fibrinogen recognition exosite in thrombin (Fenton, J. W., II, et al., *Biochemistry* 27:7106–7112, 1988; Binnie, C. G. and Lord, S. T., *Blood* 81:3186–3192, 1993; Stubbs, M. T. and Bode, W., *Thromb. Res.* 69:1–58, 1993) that is situated in an extended patch of positively charged residues in the region of the thrombin loop segment centered around Lys 70-Glu 80 (Noé, G., et al., *J. Biol. Chem.* 263:11729–11735, 1988). The exosite also binds to heparin cofactor II (Church, F. C., et al., *J. Biol. Chem.* 264:18419–18425, 1989), factor V and factor VII (Esmon, C. T. and Lollar P., *J. Biol. Chem.* 271:13882–13887, 1996) the platelet or endothelial cell thrombin receptor (Herbert, J.-M., et al., *Biochem. J.* 303:227–231, 1994), thrombomodulin (Tsiang, M., et al., *Biochemistry* 29:10602–10612, 1990; Suzuki, K. and Nishioka, J., *J. Biol. Chem.* 266:18498–18501, 1991), GPIbα (De Marco, L., et al., *J. Biol. Chem.* 269:6478–6484, 1994), as well as to a strongly anionic sequence in the carboxyl-terminal region of the leech thrombin-inhibitor, hirudin (Dodt, J., et al., *FEBS Letters* 165:180–184, 1984; Maraganore, J. M., et al., *J. Biol. Chem.* 264:8692–8698, 1989; Bourdon, P., et al., *Biochemistry* 29:6379–6384, 1990; Rydel, T. J., et al., *Science* 249:277–280, 1990; Naski, M., et al., *J. Biol. Chem.* 265:13484–13489, 1990; Parry, M. A. A., et al., *Biochemistry* 33:14807–14814, 1994).

In addition to binding to fibrinogen at its substrate site, thrombin binds to fibrin at a 'non-substrate' site(s) (Fenton, J. W., II, et al., supra, 1988; Binnie, C. G. and Lord, S. T., supra, 1993; Berliner, L. J., et al., *Biochemistry* 24:7005–7009, 1985; Kaczmarek, E. and McDonagh, J., *J. Biol. Chem.* 263:13896–13900, 1988; Vali, Z. and Scheraga, H. A., et al., *Biochemistry* 27:1956–1963, 1988). It is commonly believed that non-substrate binding takes place at the same location as fibrinogen substrate binding, namely the central E domain. As determined from binding experiments with $^{125}$I-thrombin by Liu, et al. (Liu, C. Y., et al., *J. Biol. Chem.* 254:10421–10425, 1979) two classes of non-substrate sites exist in fibrin, one of 'high' affinity ($K_a$, ~6×10$^5$M$^{-1}$) and the other of 'low' affinity ($K_a$, ~7×10$^4$M$^{-1}$). Hogg and Jackson also found two classes of sites in fibrin with affinity constants of 3.3×10$^6$ and 3.0×10$^4$, respectively (Hogg, P. J. and Jackson, C. M., *J. Biol. Chem.* 265:241–247, 1990). It has been inferred from available information that all non-substrate thrombin binding, especially that of high affinity, is in the E domain (Binnie, C. G. and Lord, S. T., supra, 1993), although to our knowledge this subject has not been specifically addressed.

Human fibrinogen is chromatographically separable into two major components ('peak 1' and 'peak 2') which differ with respect to the structure of their γ chains (Mosesson, M. W., et al., *J. Biol. Chem.* 247:5223–5227, 1972). Dimeric peak 1 fibrinogen molecules each contain two $γ_A$ chains (γ1-411V) whereas peak 2 fibrinogen molecules, which amount to ~15% of the total fibrinogen population (Mosesson, M. W. and Finlayson, J. S., *J. Lab. Clin. Med.* 62:663–674, 1963), have one $γ_A$ and one γ' chain (γ1-427L) (Wolfenstein-Todel, C. and Mosesson, M. W., *Proc. Natl. Acad. Sci. USA* 77:5069–5073, 1980; Mosesson, M. W., *Ann. NY Acad. Sci.* 408:97–113, 1983). Similar γ chain variants have been identified in rodent (Crabtree, G. R. and Kant, J. A., *Cell* 31:159–166, 1982; Legrele, C. D., et al., *Biochem. Biophys. Res. Commun.* 105:521–529, 1982) and bovine (Agnes Henschen, personal communication) fibrinogens and may exist in other animal species as well (Finlayson, J. S. and Mosesson, M. W., *Biochim. Biophys. Acta* 82:415–417, 1964). In humans, γ' chains arise through alternative processing of the primary mRNA transcript (Chung, D. W. and Davie, E. W., *Biochemistry* 23:4232–4236, 1984), and differ structurally in their C-terminal sequences in that $γ_A$ chain residues 408 to 411 are replaced in γ' chains by an anionic 20 amino acid sequence (Mosesson, M. W., supra, 1983; Wolfenstein-Todel, C. and Mosesson, M. W., *Biochemistry* 20:6146–6149, 1981). In rats (Crabtree, G. R. and Kant, J. A., supra, 1982; Homandberg, G. A., et al., *Thromb. Res.* 39:263–269, 1985) and cows (Agnes Henschen, personal communication) $γ_A$408 to 411 is replaced by a shorter but homologous sequence (see Table 1 below). The rat and human γ' chains are tyrosine-sulfated at γ' 418 (Hortin, G. L., *Biochemistry International* 19:1355–1362, 1989; Hirose, S., et al., *J. Biol. Chem.* 263:7426–7430, 1988) and also at γ' 422 in humans (Agnes Henschen, personal communication).

TABLE 1

Carboxyl-terminal sequences of γ chains and hirudin. Homologous position are outfitted

| Chain (position) | Amino Acid Sequence |
|---|---|
| human $γ_A$ (408–411) | A G D V |
| human γ' (408–427) | V R P [E] [H] P A [E] T [E] [Y] E S L Y P E D D L |
| rat γ' (408–419) | V S V [E] [H] E V [D] V [E] [Y] P |
| bovine γ' (408–419) | V R V [E] [H] H V [E] I [E] [Y] D |
| hirudin (53–65) | N G D F E E I P E [E] [Y] L Q |

$γ_A$ and γ' chains are functionally equivalent with respect to factor XIIIa-catalyzed crosslinking (Wolfenstein-Todel, C. and Mosesson, M. W., supra, 1980), but unlike the $γ_A$ chain, γ' chains lack the complete platelet binding sequence, γ'$_A$400–411, and therefore do not support ADP-induced fibrinogen binding or platelet aggregation (Harfenist, E. J., et al., *Blood* 64:1163–1168, 1984; Kirschbaum, N. E., et al., *Blood* 79:2643–2648, 1992; Farrell, D. H. and Thiagarajan, P., *J. Biol. Chem.* 269:226–231, 1994). Siebenlist, et al. has recently presented evidence that plasma factor XIII binds specifically to γ' chains (Siebenlist, K. R., et al., *Biochemistry*, 35:10448–10453, 1996), but little else is known about its functions.

In other studies, workers have investigated the relationship between hirudin and thrombin inhibition. Hirudin is a naturally occurring polypeptide produced in the salivary glands of the blood sucking leech *Hirudo medicinalis*. Hirudin is a potent anticoagulant which binds tightly to thrombin in a two-step process. Initially hirudin binds, via its carboxyl-terminal 53–65 amino acid residues (hirugen), to the anion-binding exosite of thrombin. Subsequently, the amino-terminal region of hirudin binds to the catalytic site of thrombin. Numerous artificial constructs have been devised to mimic the inhibitory action of hirudin, such as hirulog and hirutonin. These hirudin-analogues are comprised of an amino-terminal segment, which binds the catalytic site of thrombin, linked to the hirugen sequence. The various analogues (hirulog 1, hirutonin 2, etc.) result from substitutions in each of these segments in different combinations.

In the Examples below we present compelling evidence that the anionic carboxy-terminal γ' chain sequence situated in the fibrin D domain constitutes the high-affinity thrombin binding site, which is itself separate and distinct from the low affinity thrombin binding sites that reside in the central E domain. This finding has relevance in terms of designing an improved thrombin inhibitor.

SUMMARY OF THE INVENTION

The present invention is a thrombin inhibitor comprising a means for inactivating or sequestering thrombin and a portion of the fibrinogen γ' chain that binds at the anion-binding exosite of thrombin.

In one embodiment, this inhibitor comprises three segments. The first segment binds at the catalytic site of thrombin, the second segment connects the first segment and the third segment, and the third segment comprises a portion of the fibrinogen γ' chain that binds at the anion-binding exosite of thrombin.

The three segments comprising the thrombin inhibitor may be a naturally occurring molecule or may be the result of genetic engineering. The second segment and the first or third segment may be naturally part of the same molecule.

In one preferred form of the invention, the third segment comprises amino acids selected from residues 408–427 of the fibrinogen human γ' sequence. In a more advantageous embodiment of the present invention, the third segment comprises amino acids 410–427 of the native γ' sequence. In a most advantageous embodiment, the third segment comprises amino acids 414–427.

In another preferred embodiment of the present invention, the first segment comprises a plasminogen activator moiety or a platelet receptor antagonist.

In another embodiment, the present invention is a composition comprising an amount of the inhibitor effective for inhibiting a thrombin-mediated function in a patient or an extracorporeal blood in a pharmaceutical acceptable carrier.

In another embodiment, the invention is a recombinant genetic construct comprising nucleic acid sequences encoding the inhibitor.

It is an object of the present invention to provide a thrombin inhibitor comprising the human γ' sequence.

It is another object of the present invention to provide an improved thrombin inhibitor.

It is another object of the present invention to provide a pharmaceutical composition with thrombin inhibition properties.

It is another object of the present invention to provide a recombinant gene construct suitable to produce the thrombin inhibitor.

Other objects, features and advantages of the present invention will become apparent after one studies the specification, claims and drawings.

DESCRIPTION OF THE INVENTION

1. In General

Figure 1:
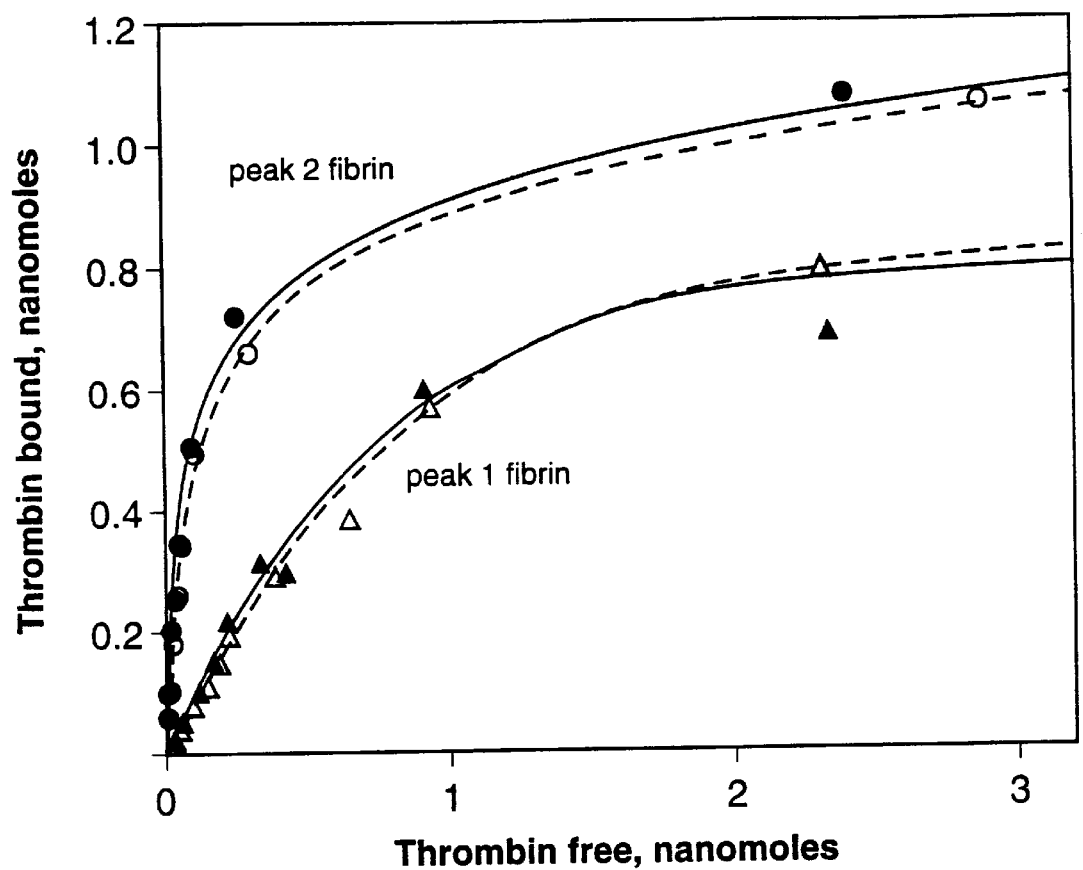
FIG. 1 is a graph of $^{125}$I PPACK-thrombin binding to factor XIIIa-crosslinked (●; —) and non-crosslinked (○; ---) peak 1 or peak 2 fibrin.

The present invention is a thrombin inhibitor which comprises a means for inactivating or sequestering thrombin and a portion of the human γ' sequence that binds at the thrombin anion-binding exosite. In one embodiment, the invention comprises a sequence of amino acids found in residues 408–427 of the fibrinogen γ' sequence.

The Examples below demonstrate that the anionic carboxy-terminal γ' chain sequence situated in the fibrin D domain constitutes the high affinity thrombin binding site and is separate and distinct from the low affinity thrombin binding sites that reside in the central E domain. We envision that this high affinity binding site can be advantageously used to develop a thrombin inhibitor. Such an inhibitor could be useful in the treatment or prevention of vascular diseases, such as intravascular thrombosis, unstable angina pectoris, myocardial infarction, or stroke.

2. Characterization of the Three Segments

In one embodiment, the present invention is a thrombin inhibitor comprising three segments. The thrombin inhibitor may comprise a naturally occurring molecule or a segment of a naturally occurring molecule or may comprise a genetically engineered molecule combining two or more amino acid or nucleotide segments that are not naturally connected. Additionally, the first and second segments or second and third segments may be part of the same naturally occurring molecule.

First Segment

In one embodiment of the present invention, the first segment of the thrombin inhibitor binds at the catalytic site of thrombin located at or near Ser-195 and inhibits or retards the amidolytic or esterolytic activity of thrombin. The amino acid residues of the first segment may bind reversibly to thrombin and be slowly cleaved, may bind reversibly to thrombin and not be cleaved, or may bind irreversibly to thrombin.

One of skill in the art would be aware of several thrombin catalytic site inhibitors which would result in effective thrombin inhibitors when coupled to the γ' sequence. Examples of inhibitors include but are not limited to:

(D)-Phe-Pro-Arg-; Acetyl-(D)-Phe-Pro-Arg-Pro-(hirutonin-2); BMS-183507; FPA 7-20 (as in hirulog 2); and Argatroban (Texas Biotech, Tex., also called argipidine).

In another embodiment of the thrombin inhibitor invention, the first segment does not inactivate thrombin directly by inhibiting the catalytic site, but functions in other ways and sequesters thrombin when the first segment is linked to the γ' sequence. For example, use of plasminogen activator moieties as a first segment would result in activation of fibrinolysis. In combination with a third segment which would bind thrombin, one will have created a thrombin inhibitor. One preferred first segment moiety of this type includes recombinant single chain urokinase plasminogen activators (rscu-PA) (Steffens, G. J., et al., German Patent Office, DE 4323754C1) such as the following: M23 is a 40 kDa segment of rscu-PA coupled to the C-terminal hirugen sequence (Schneider, J., et al., *Eur. J. Pharmac.* 302:69–77, 1996). Another preferred moiety is tissue plasminogen activator (t-PA) coupled to a thrombin binding moiety as described below.

Other envisioned first segments include platelet receptor (GPIIb/IIIa) antagonists which would inhibit platelet aggregation and platelet activation when coupled with a thrombin inhibiting γ' sequence. Preferred platelet-binding antagonists include the amino acid sequence RGDS (Church, F. C., et al., *J. Biol. Chem.* 266:11975–11979, 1991), RGDS analogues (orally active) such as Smithkline Beecham 214947 or Hoechst S1762, and c7E3 (mouse/human chimera anti-IIbIIIa) (Revierter, J. C., et al., *J. Clin. Invest.* 98:8630874, 1996).

Second Segment

The second segment of the three segment thrombin inhibitor principally links the first and third segments. Therefore, it is the length of the second segment, rather than its composition, that is important. Preferably, the calculated length of the backbone chain which characterizes the linker should be at least about 18 Å and less than about 42 Å. This length bridges the distance between the catalytic site and the exosite of thrombin.

For "hirulog 1" (which requires a similar linker) the linker comprises four glycine residues. Hurutonin-6 uses —[[CH$_2$]]$_4$—C(O)]—[NH—CH$_2$—CH=CH—CH$_2$—C(O)]$_2$-Pro-Leu.

Alternatively, one might use a "trivalent" inhibitor (for example, QSHNDG) in which the second segment is more than a linker in that it would also interact with thrombin and thereby increase the affinity of the first and third segments (Szewczuk, Z., et al., *Biochemistry* 32:3396–3404, 1993).

Another thrombin inhibitor (known as hirutonin-2) has used the hirudin sequence, hir 48–52, which is adjacent to hir 53–65 and which could serve as a second segment spacer linking segments 1 and 3. It is likely that a similar strategy of using a sequence proximal to γ' 414–427 (i.e., 410–413) could serve as a linker and be equivalent to linking the first segment to a longer third segment.

Third Segment

The third segment of the thrombin inhibitor comprises an amino acid sequence derived from residues 408–427 of the fibrinogen γ' sequence. By "fibrinogen γ' sequence" we mean the human fibrinogen γ' sequence described in Table 1 and its conservative-substitution equivalents.

Most preferably, the third segment comprises residues 414–427. Other preferable segments include 414–425, 414–426, and 415–426. Also preferably, the Tyr residues have been sulfated, as described below in the Examples.

Also preferably, residue 420 serine has been altered to an alanine and residue 416 threonine has been altered to a valine. These alterations prevent sulfation of the naturally occurring hydroxylated threonine and serine residues.

It is known by those of skill in the art of molecular biology that conservative changes may be made in an amino acid sequence and that the modified amino acid sequence may retain the same functional properties as the original sequence. The present invention is meant to encompass such conservative amino acid changes. For example:

Preferably the anion-binding exosite sequence (γ' 414–427) has the formula:

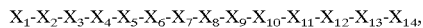

$$X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13}\text{-}X_{14},$$

where $X_1$ is a nonpolar amino acid; $X_2$ is an anionic amino acid; $X_3$ is a polar or nonpolar amino acid; $X_4$ is an anionic amino acid; $X_5$ is Tyr; $X_6$ is an anionic amino acid; $X_7$ is a polar or nonpolar amino acid; $X_8$ is a nonpolar amino acid; $X_9$ is Tyr; $X_{10}$ is Pro, $X_{11}$ is an anionic amino acid; $X_{12}$ is an anionic amino acid; $X_{13}$ is an anionic amino acid; and $X_{14}$ is a nonpolar amino acid.

3. Preparation of the Thrombin Inhibitor a. Standard solid phase peptide synthesis methodology The thrombin inhibitor of the present invention may be synthesized by solid phase peptide synthesis, enzymatic cleavage of natural or recombinant fibrin, solution phase peptide synthesis, organic chemical synthesis techniques or a combination of these techniques known to one of skill in the art.

Cyclic peptides have been shown to fix the conformation and enhance the presentation of peptides. This is a relevant consideration in designing bioactive peptides.

b. Recombinant genetic construct

In a preferred embodiment of the present invention, one would manufacture the thrombin inhibitor by creating a recombinant genetic construct encoding each of the three segments. Preferably, this construct would link all three segments so that they could be transcribed in a functionally correct order. One of skill in the art of molecular biology would recognize the elements needed in such a genetic construct, such as an adequate promoter and transcription terminator. One could obtain sequences encoding the segments by analyzing the necessary amino acid sequences and determining the requisite nucleotide sequence. These nucleotide sequences could be artificially synthesized or obtained from clones of a naturally occurring sequence.

4. Pharmaceutical Reaqents

The present invention is also a pharmaceutically acceptable reagent comprising the thrombin inhibitor and a pharmaceutically acceptable carrier. These inhibitors may be formulated using conventional methods to prepare pharmaceutically useful compositions and may be employed for treating or preventing thrombotic diseases in a patient.

EXAMPLES

Example 1

Identification and Characterization of the Thrombin-binding Sites on Fibrin

1. In General

Thrombin binds to fibrin at two classes of nonsubstrate sites, one of high affinity and the other of low affinity. We investigated the location of these thrombin binding sites by assessing the binding of thrombin to fibrin lacking or containing γ' chains, which are fibrinogen γ chain variants that contain a highly anionic carboxy-terminal sequence. We found the high affinity thrombin binding site to be located exclusively in D domains on γ' chains ($K_a$, 4.9×10$^6$M$^{-1}$; n, 1.05 per γ' chain), whereas the low affinity thrombin binding site was in the fibrin E domain ($K_a$, $0.29\times10^6 M^{-1}$; n, 1.69 per molecule). The amino-terminal β15-42 fibrin sequence is an important constituent of low affinity binding, since thrombin binding at this site is greatly diminished in fibrin molecules lacking this sequence. The tyrosine-sulfated, thrombin exosite-binding hirudin peptide, S-Hir$^{53-64}$ (hirugen), inhibited both low and high affinity thrombin binding to fibrin ($IC_{50}$ 1.4 μM and 3.0 μM, respectively). The presence of the high affinity γ' chain site on fibrinogen molecules did not inhibit fibrinogen conversion to fibrin as assessed by thrombin time measurements, and thrombin exosite binding to fibrin at either site did not inhibit its catalytic activity toward a small thrombin substrate, S-2238. We infer from these findings that there are two low affinity non-substrate thrombin binding sites, one in each half of the dimeric fibrin E domain, and that they may represent a residual aspect of thrombin binding and cleavage of its substrate fibrinogen. The high affinity thrombin binding site on γ' chains is a constitutive feature of fibrin as well as fibrinogen.

2. Materials and Methods

The abbreviations employed are:GPIBα, glycoprotein Ibα; PPACK, D-Phe-pro-arg chloromethyl ketone; S-2238, H-D-Phenylalanyl-L-pipecolyl-L-arginine-p-nitroanilide dihydrochloride; PEG 8000, polyethylene glycol, average molecular weight 8000; S-Hir$^{53-64}$, sulfated carboxyl-terminal residues 53 to 64 of hirudin; des Bβ1-42 fibrinogen, fibrinogen from which the amino-terminal 4 residues of the Bβ chain have been cleaved; β15-42, amino-terminal fibrin β chain sequence.

Human fibrinogen fraction I-2 was isolated from normal citrated plasma by glycine precipitation (Mosesson, M. W. and Sherry, S., Biochemistry 5:2829–2835, 1966) and separated into peaks 1 and 2 fibrinogen by anion exchange chromatography on DEAE cellulose (Siebenlist, K. R., et al., supra, 1996). Des Bβ1-42 fibrinogen was produced from peak 1 or peak 2 fibrinogen by digestion with crotalus atrox protease III (Pandya, B. V., et al., Biochemistry 30:162–168, 1991). Fibrinogen concentrations were determined spectrophotometrically at 280 nm using an absorbance coefficient of 1.51 ml mg$^{-1}$ cm$^{-1}$ (Mosesson, M. W. and Finlayson, J. S., supra, 1963). Molecular weights of 340,000 and 325,000 were used for fibrinogen and des Bβ1-42 fibrinogen, respectively (Pandya, B. V., et al., supra, 1991; Henschen, A., et al., Ann. NY Acad. Sci. 408:28–43, 1983).

Fibrin-SEPHAROSE resin was prepared by coupling CNBr-activated SEPHAROSE resin with peak 2 fibrinogen and then converting the resin-bound fibrinogen to fibrin in the presence of thrombin (2 u/ml) for 16 hours at 4° C. as described by Heene and Mathias (Heene, D. L. and Matthias, F. R., Thromb. Res. 2:137–154, 1973). The fibrin-SEPHAROSE was washed with 1.0M NaCl, 50 mM HEPES pH 7.4 buffer, followed by 100 mM NaCl, 50 mM HEPES pH 7.4 buffer containing 50 mM $CaCl_2$ and 2 mM phenylmethylsulfonyl fluoride.

Human α-thrombin (specific activity, 3.04 u/μg) was obtained from Enzyme Research Laboratories, Inc., South Bend, Ind. A molecular weight of 36,500 and an absorbance coefficient of 1.83 ml mg$^{-1}$ cm$^{-1}$ were used for calculating thrombin concentrations (Fenton, J. W., II, et al., J. Biol. Chem. 252:3587–3598, 1977). PPACK-thrombin was prepared by adding a five-fold molar excess of PPACK (Calbiochem, San Diego, Calif.) to α-thrombin and after dialysis the mixture was labeled with $^{125}I$ (Martin, B. E., et al., Biochemistry 15:4886–4893, 1976). The labeled protein was separated from free iodine by affinity chromatography on peak 2 fibrin-SEPHAROSE CL-4B that had been equilibrated with 50 mM HEPES, 100 mM NaCl, pH 7.4 buffer containing 0.01% (w/v) PEG 8000. Elution of thrombin was achieved with HEPES buffer pH 7.4, containing either 500 mM NaCl or 40 mM $CaCl_2$.

Factor XIII (1.95 u/μg) was prepared from pooled human plasma (Lorand, L. and Gotoh, T.; in Methods in Enzymology pp. 770–782, Academic Press, New York, 1970) and the activity assayed by the method of Loewy, et al. (Loewy, A. G., et al., J. Biol. Chem. 236:2625–2633, 1961). Factor XIII (500 u/ml) in 100 mM NaCl, 50 mM HEPES pH 7.4, was activated to XIIIa in the presence of 500 μM dithiothreitol and 10 mM $CaCl_2$ by incubation with thrombin (10 u/ml, final) for 30 minutes at 37° C. (Kanaide, H. and Shainoff, J. R., J. Lab. Clin. Med. 85:574–597, 1975).

Thrombin-fibrin binding experiments were performed using a modification of the method reported by Liu, et al. (Liu, C. Y., et al., supra, 1979). Fibrin monomer solutions were prepared from fibrinogen clotted at 1 mg/ml in 60 mM $NaH_2PO_4$ buffer, pH 6.4, with thrombin (1 u/ml, final) for two hours at room temperature. The clots were synerized and dissolved in 20 mM acetic acid to >10 mg/ml fibrin, and repolymerized in a 10-fold excess of 100 mM NaCl, 50 mM tris, pH 7.4 buffer containing 40 mM $CaCl_2$, and 2 mM N-ethylmaleimide. These clots were synerized and dissolved in 20 mM acetic acid to a 10 mg/ml stock solution. Clots containing 0.5 or 1 nmole fibrin were formed by adding a fibrin monomer solution to a 100 mM NaCl, 50 mM HEPES, 0.01% (w/v) PEG 8000, pH 7.4 buffer containing varying amounts of $^{125}I$-labeled PPACK-thrombin, and incubated for 2 hours at room temperature. Clot-bound thrombin was separated from free thrombin by syneresis of the clot. The final concentration of reactants in the clotting mixture were fibrin, 2.5 μM, $^{125}I$ PPACK-thrombin, 0 to 37.5 μM, in a final volume of 200 or 400 μl. For clotting mixtures containing des Bβ1-42 fibrin, which polymerizes slowly and incompletely, full clot recovery (>95%) was assured by crosslinking the fibrin with factor XIIIa (25 u/ml) for 2 hours at room temperature. After the incubation period, tubes were centrifuged and thrombin-bound clots separated from free thrombin by syneresis. The distribution of thrombin bound to the clot and free in solution was determined by radioactivity counting in a Packard Multi-prias 3 gamma counter. The amount of thrombin trapped in the clot was estimated from the radioactive counts that were retained in crosslinked clots of peak 1 or des Bβ1-42 peak 1 fibrin in the presence of 25 pM S-Hir$^{53-64}$, which had been added to block thrombin exosite binding to fibrin.

The binding data were graphed as Scatchard plots (Scatchard, G., Ann. NY Acad. Sci. 51:660–672, 1949). Data indicating a two-component system were deconvoluted by the method of Klotz and Hunston (Klotz, I. M. and Hunston, D. L., Biochemistry 10:3065–3069, 1971). It was not technically feasible to reach thrombin concentrations which saturated the low affinity site in samples of peak 2 fibrin that contained high levels of the high affinity component. In these experiments, the low affinity component was defined by peak 1 ($\gamma_A, \gamma_A$) fibrin values, and was used for correcting high affinity values (Klotz, I. M. and Hunston, D. L., supra, 1971). High affinity thrombin binding to des Bβ1-42 peak 2 fibrin was not significantly affected by a low affinity binding component and these data were therefore not corrected. The level of thrombin entrapment in the clots (~4% of total counts) did not significantly effect binding parameters, and therefore no corrections were applied to the data.

Competitive binding experiments involving thrombin anionic exosite binding were performed with the sulfated hirudin peptide, S-Hir[53-64], which was a generous gift from Dr. John Maraganore of Biogen Inc., Cambridge, Mass. Hirugen at concentrations up to 40 μM was added to $^{125}$I PPACK-thrombin (1 μM) and 0.5 nmoles fibrin at a final volume of 200 μl as described above for thrombin binding measurements. Peptide concentrations were estimated spectrophotometrically at 215 nm using an absorbance coefficient of 15.0 ml $mg^{-1}$ $cm^{-1}$ (Scopes, R. K., *Protein Purification*, Springer-Verlag, New York, 1982).

A Fibrometer Precision Coagulation Timer (BBL) was used to determine the thrombin time for the conversion of fibrinogen (1 mg/ml final) to fibrin in 50 mM Tris, 100 mM NaCl, pH 7.4 at 37° C. at a thrombin level of 0.6 u/ml. Hydrolysis of S-2238 (H-D-Phenylalanyl-L-pipecolyl-L-arginine-p-nitroanilide dihydrochloride; Chromogenix, M ölndal, Sweden) by thrombin (3.2 nM) in 0.10M NaCl, 0.05M Tris, pH 7.5 buffer, was monitored at 405 nm at room temperature. Samples contained S-2238 (50 μM), with or without peak 1 fibrin (1 μM), or peak 2 fibrin (1 μM). The hydrolysis rate was estimated from the increase in absorbance at 405 nm during the first three minutes of the reaction.

3. Results

Thrombin binding to fibrin—In our studies of thrombin binding to fibrin we found it useful as a general condition to covalently crosslink the fibrin polymer in the presence of factor XIIIa during the binding experiment in order to assure complete fibrin recovery (>95%). This procedure was particularly useful for recovering des Bβ1-42 fibrin clots, which polymerize slowly and incompletely in the absence of crosslinking (Siebenlist, K. R., et al., *J. Biol. Chem.* 265:18650–18655, 1990). There were no significant differences in thrombin binding behavior to crosslinked and non-crosslinked fibrin (see FIG. 1), confirming the findings of Liu, et al. (Liu, C. Y., et al., *J. Biol. Chem.* 255:7627–7630, 1980). Thrombin entrapment in the clot, as assessed in the presence of 25 μM S-Hir[53-64], was ~4% of the total counts and did not significantly change any of the calculated binding parameters.

FIG. 1 is a graph of $^{125}$I PPACK-thrombin binding to factor XIIIa-crosslinked (●; __) and non-crosslinked (○; ---) peak 1 or peak 2 fibrin. The curves represent the mean values of 3 to 6 separate experiments for each condition. The regression coefficients for the curves ranged from 0.91–0.98.

Figure 2:
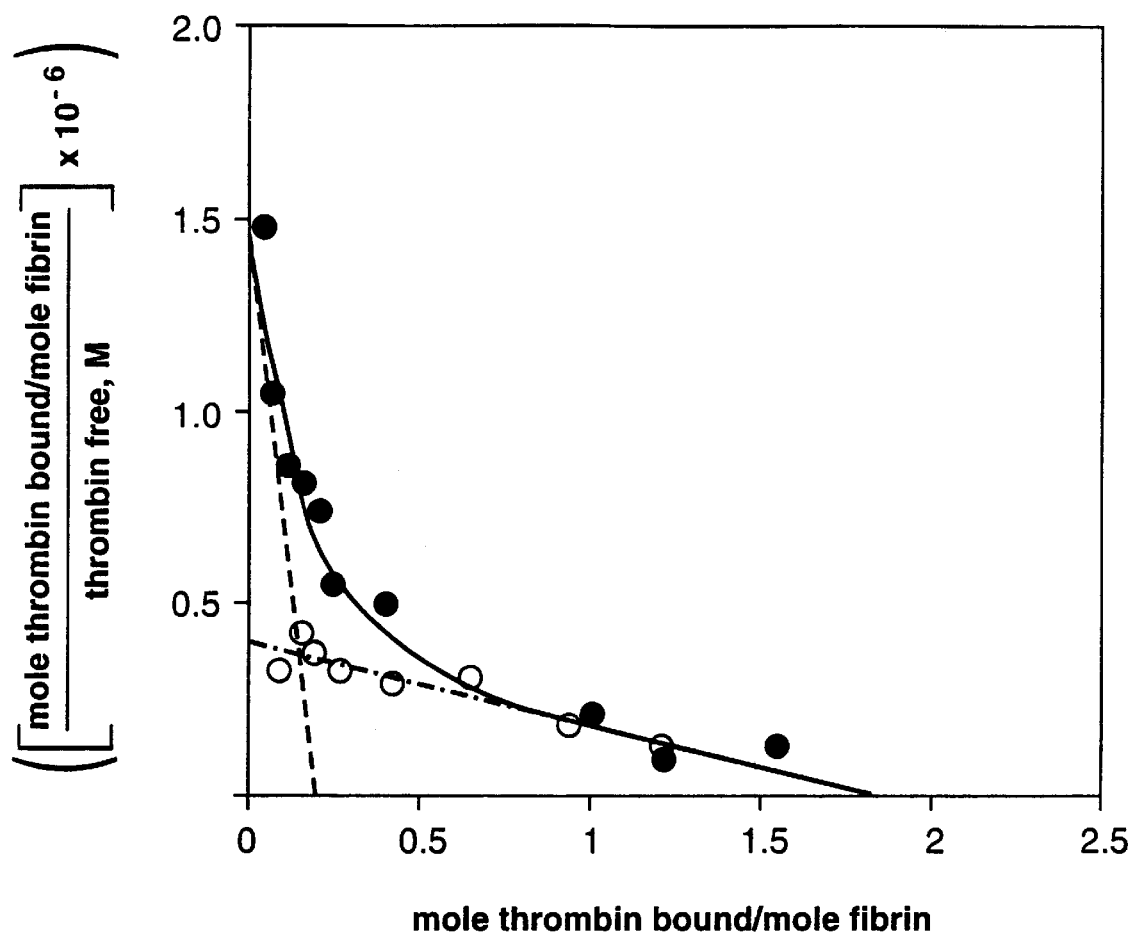
FIG. 2 is a Scatchard analysis of the binding of $^{125}$I PPACK-thrombin to fraction I-2 fibrin (●) or peak 1 fibrin (○).

Low and high affinity binding sites—Our previous study with des Bβ1-42 fibrin had indicated that the β15-42 sequence was a component of the non-substrate thrombin binding site in the fibrin E domain (Siebenlist, K. R., et al., supra, 1990). To extend those observations we carried out a systematic study of non-substrate thrombin binding to several fibrin preparations which differed with respect to their γ chain composition, their Bβ1-42 content, or both. Fraction I-2 fibrin, which has 15% γ'-containing molecules (Mosesson, M. W. and Finlayson, J. S., supra, 1963) was studied first (see FIG. 2). FIG. 2 is a Scatchard analysis of the binding of $^{125}$I PPACK-thrombin to fraction I-2 fibrin (●) or peak I fibrin (○). The dashed line (- - -) represents the slope of the high affinity binding component in fraction I-2 fibrin. The broken line (- • - • -) represents the slope of the low affinity component in peak 1 fibrin.

As assessed from the Scatchard plot, our results correspond to those reported by Liu, et al. (Liu, C. Y., et al., supra, 1979), who studied a similar fibrinogen subfraction. The data indicate two classes of binding sites, one of high affinity ($K_a$, $5.5 \times 10^6 M^{-1}$) and the other of low affinity ($K_a$, $0.45 \times 10^6 M^{-1}$) (Table 2).

TABLE 2

| Fibrin Fraction | High Affinity Site* | | | Low Affinity Site† | | |
| --- | --- | --- | --- | --- | --- | --- |
| | n | $K_a \times 10^{-6} \pm$ sd ($M^{-1}$) | no. sites/mole ± sd | n | $K_a \times 10^{-6} \pm$ sd ($M^{-1}$) | no. sites/mole ± sd |
| fraction I-2 | 4 | 5.5 ± 1.3 | 0.22 ± 0.02 | 4 | 0.21 ± 0.05 | 1.60 ± 0.20 |
| peak 1 | 8 | 0 | 0 | 8 | 0.21 ± 0.05 | 1.80 ± 0.23 |
| peak 2 | 6 | 5.6 ± 0.8 | 0.83 ± 0.12 | 3 | indeterminate | indeterminate |
| des Bβ1-42 peak 1 | 4 | 0 | 0 | 4 | 0.11 ± 0.03 | 1.66 ± 0.34 |
| des Bβ1-42 peak 2 | 6 | 4.2 ± 0.8 | 0.78 ± 0.11 | 6 | indeterminate | indeterminate |

*The mean $K_a$ for the high affinity site based on all determinations (n = 16) is 4.9 ± 1.2 × $10^6 M^{-1}$, with 1.05 ± 0.27 thrombin binding sites per γ' chain.
†The mean $K_a$ for the low affinity site based on all determinations (n = 12) is 0.29 ± 0.14 × $10^6 M^{-1}$, with 1.69 ± 0.25 thrombin binding sites per fibrin molecule.

Studies of thrombin binding to peak 1 fibrin, which contains only $γ_A$ chains, indicated a single class of binding site with a $K_a$ of $0.21 \times 10^6 M^{-1}$, corresponding to the low affinity site in fraction I-2 fibrin, and having a binding stoichiometry of 1.80 per molecule of fibrin (FIG. 2). Parallel analysis of thrombin binding to peak 2 fibrin demonstrated that high affinity binding dominated the Scatchard plot and that there were 0.83 high affinity sites per fibrin molecule (see FIG. 3), a stoichiometry that corresponds well to the γ'-chain content in peak 2 fibrinogen preparations (48% γ', 52% $γ_A$) (Stathakis, N. E., et al., *Thromb. Res.* 13:467–475, 1978). Low affinity binding in peak 2 fibrin was too low for accurate quantitation, but was in the same range as was found for peak 1 or fraction I-2 fibrin.

Figure 3:
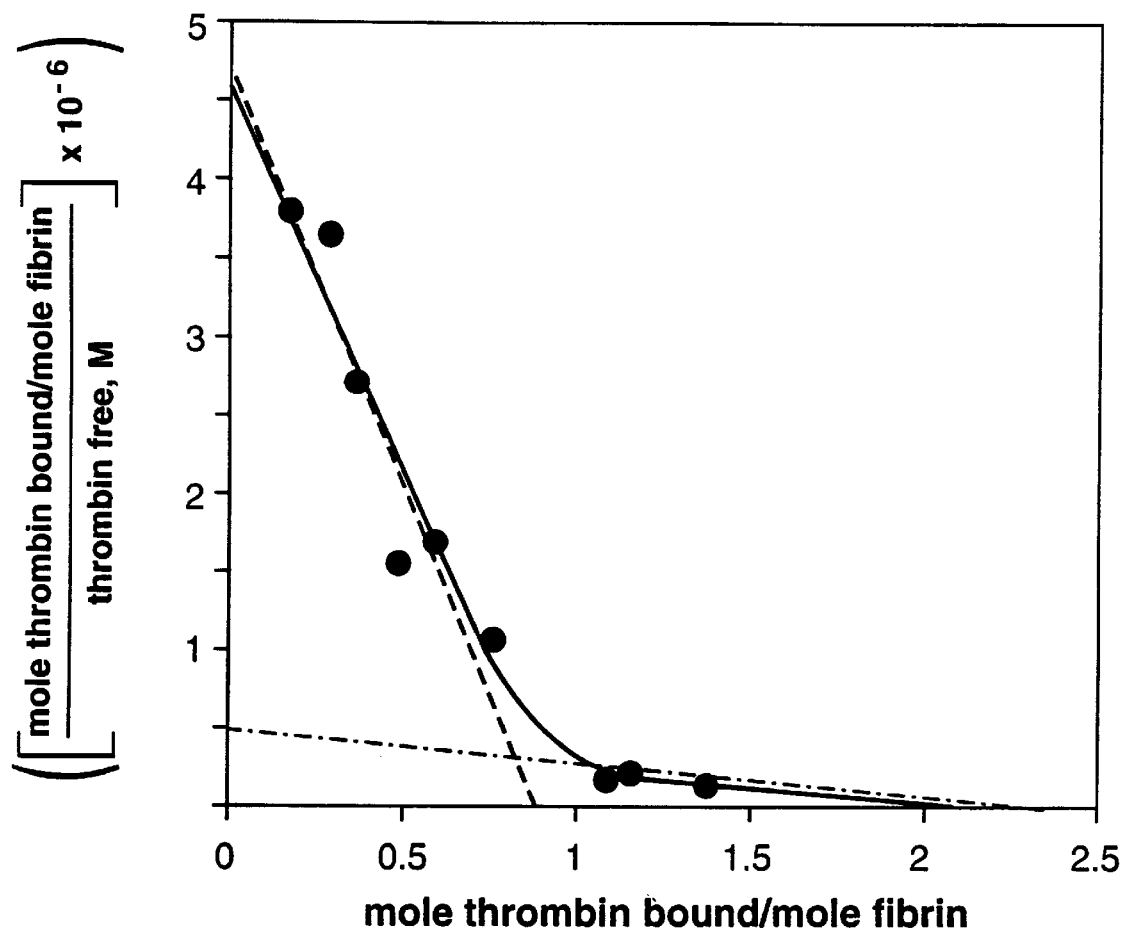
FIG. 3 is a Scatchard analysis of the binding of $^{125}$I PPACK-thrombin to peak 2 fibrin.

FIG. 3 is a Scatchard analysis of the binding of $^{125}$I PPACK-thrombin to peak 2 fibrin. The dashed line (- - -) represents the slope of the high affinity component in peak 2 fibrin. The low affinity component, determined from the low affinity binding component of peak 1 fibrin, is represented by the broken line (- • - • -).

There was a marked reduction of low affinity binding to des Bβ1-42 peak 2 fibrin (see FIG. 4), and therefore no corrections to the high affinity values were applied for the presence of a low affinity component.

Figure 4:
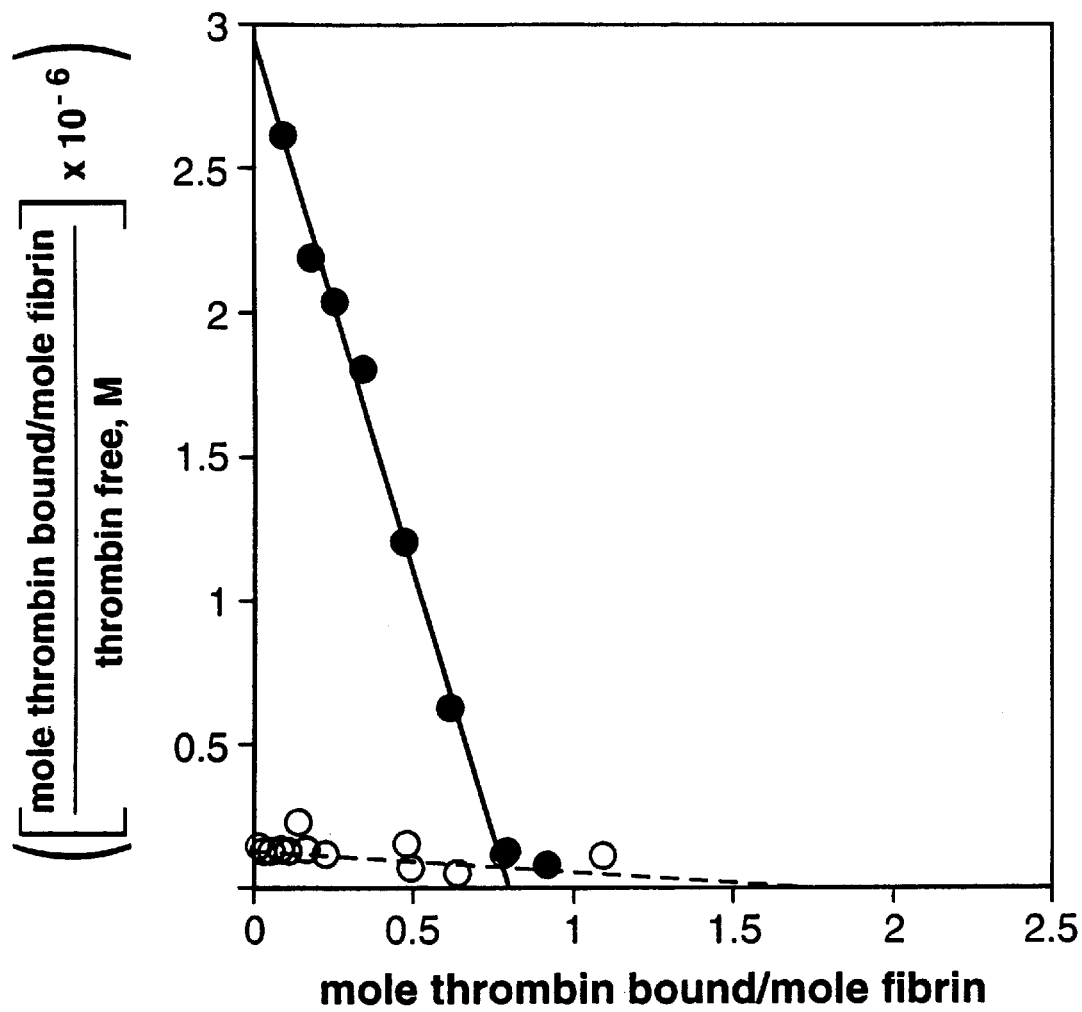
FIG. 4 is a Scatchard analysis of the binding of $^{125}$I PPACK-thrombin to des Bβ1-42 peak 2 fibrin, (●) or des Bβ1-42 peak 1 fibrin (○).

FIG. 4 is a Scatchard analysis of the binding of $^{125}$I PPACK-thrombin to des Bβ1-42 peak 2 fibrin, (●) or des Bβ1-42 peak 1 fibrin (○). The solid line represents the high affinity component. The low affinity component, is represented by the broken line (- • - • -).

In the case of des Bβ1-42 peak 1 fibrin, which lacks a high affinity binding site, reduced levels of low affinity thrombin binding were found (FIG. 4) and exceeded the amount that could be attributed to entrapment alone. The estimated $K_a$ ($0.11 \times 10^6 M^{-1}$) was 38% of that found for peak 1 or fraction I-2 fibrin, but the stoichiometry was the same (i.e., 1.66 sites per molecule).

Thrombin exosite-binding peptide—To provide additional evidence that the γ' sequence contains the high affinity site for thrombin exosite binding, we evaluated thrombin binding in the presence of S-Hir[53-64], a well-characterized thrombin exosite-binding peptide, to des Bβ1-42 peak 2 (high affinity) or peak 1 (low affinity) fibrin. S-Hir[53-64] was an effective competitive inhibitor of thrombin binding to fibrin with an $IC_{50}$ of 3.0 μM for high affinity thrombin binding and 1.4 μM for low affinity binding (FIG. 5), thus indicating that both classes of sites bind thrombin through its exosite.

Figure 5:
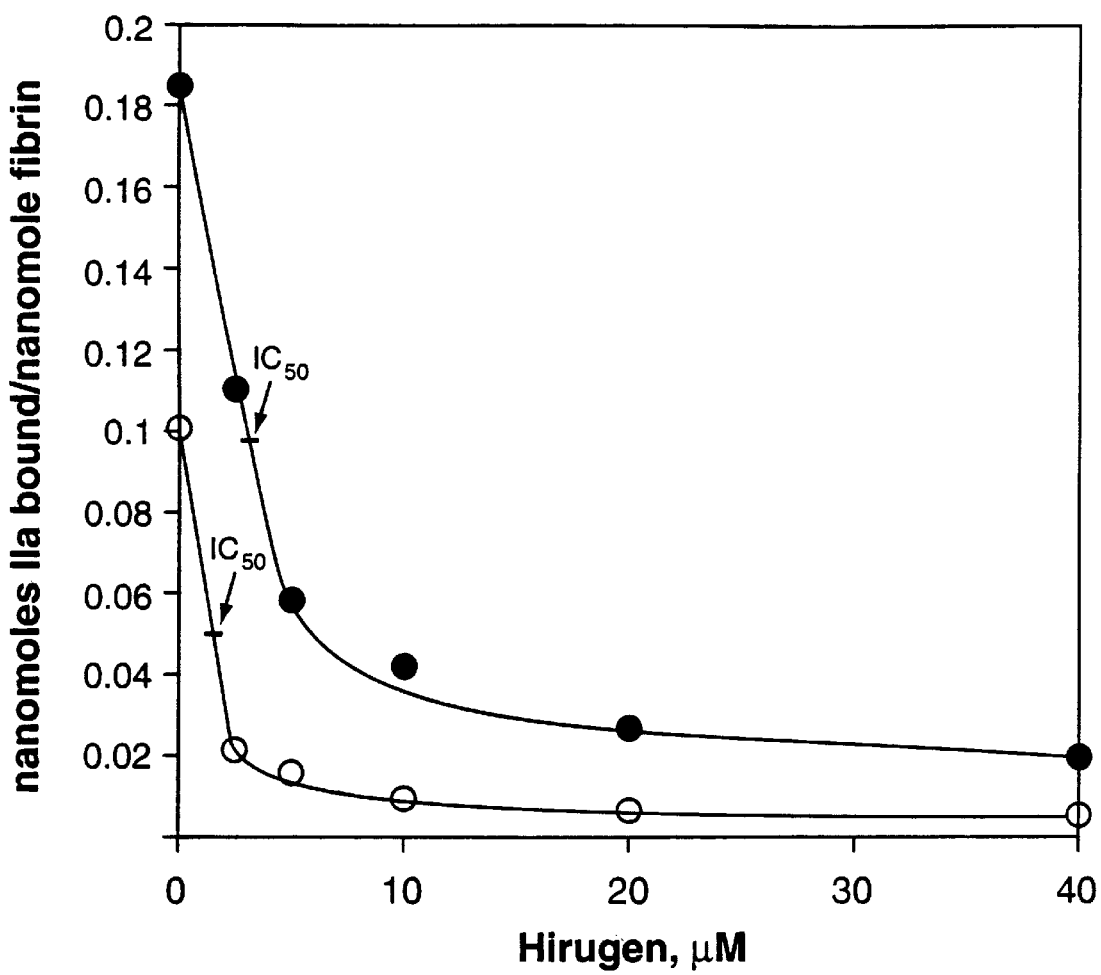
FIG. 5 is a graph of S-Hir$^{53-64}$ (hirugen) inhibition of $^{125}$I PPACK-thrombin binding to des Bβ1-42 peak 2 fibrin (●) or peak 1 fibrin (○).

FIG. 5 is a graph of S-Hir$^{53-64}$ (hirugen) inhibition of $^{125}$I PPACK-thrombin binding to des Bβ1-42 peak 2 fibrin (●) or peak 1 fibrin (○). The calculated IC$_{50}$ for each curve is indicated.

Fibrinogen to fibrin conversion and S-2238 hydrolysis— The mean thrombin times for peak 1 and peak 2 fibrinogens were 20.5±0.5 seconds and 20.4±0.5 seconds (n=5), respectively, indicating that the presence of the γ' sequence had no measurable effect on thrombin substrate cleavage of fibrinogen. Hydrolysis of S-2238 was not inhibited by the presence of peak 1 fibrin or peak 2 fibrin in the hydrolysis mixture (Table 3).

TABLE 3

Thrombin Hydrolysis of S-2238

| Substrate | n | Initial rate CA$_{405\ nm}$/minute |
|---|---|---|
| S-2238 alone | 8 | 0.12 ± 0.01 |
| S-2238 + peak 1 fibrin | 8 | 0.13 ± 0.02 |
| S-2238 + peak 2 fibrin | 9 | 0.11 ± 0.01 |

4. Discussion

These present experiments show that there is a unique high affinity non-substrate binding site for thrombin in the carboxy-terminal region of the γ' chain and a low affinity class of binding site in the amino-terminal region of fibrin, the latter contained in part within the Bβ1-42 sequence. In studies of fraction I-2 fibrinogen, which contains approximately 8% γ' chains, we detected the same two classes of binding sites that were identified by Liu, et al. (Liu, C. Y., et al., supra, 1979). The binding affinities we determined were about ten-fold higher for high affinity binding and four-fold higher for low affinity binding (Table 2). In peak 1 fibrin (γ$_A$, γ$_A$) only the low affinity binding component was observed, whereas with peak 2 fibrin (γ', γ$_A$), there was increased high affinity thrombin binding corresponding to the increased content of γ' chains. Overall, high affinity binding stoichiometry corresponds well to the content of γ' chains, with one thrombin per γ' chain.

Although the existence and structure of the γ' chain has been known for many years (Mosesson, M. W., et al., supra, 1972; Wolfenstein-Todel, C. and Mosesson, M. W., supra, 1980; Stathakis, N. E., et al., supra, 1978), its role as the high affinity non-substrate thrombin binding site in fibrin has been overlooked for several reasons. First, it has been generally assumed that the entire thrombin binding site in fibrin was a residual of the substrate recognition site in fibrinogen. Thus, knowledge that there were two classes of binding sites in fibrin, coupled with the observation that high affinity thrombin binding was only a minor component of the total binding reaction in fraction I-2 fibrin (Liu, C. Y., et al., supra, 1979; Hogg, P. J. and Jackson, C. M., supra, 1990), evidently did not raise suspicion of another possible thrombin-binding location. Second, most investigations on this subject have involved only central E domain structures (Kaczmarek, E. and McDonagh, J., supra, 1988; Vali, Z. and Scheraga, H. A., supra, 1988; Hogg, D. H. and Blombäck, B., *Thromb. Res.* 12:953–964, 1978; Binnie, C. G. and Lord, S. T., *Thromb. Haemost.* 65:165–168, 1991) or in addition, plasmic D fragments (Kaczmarek, E. and McDonagh, J., supra, 1988; Vali, Z. and Scheraga, H. A., supra, 1988) from which the γ' sequence had most likely been cleaved (Haidaris, P. J., et al., *Blood* 74:2437–2444, 1989) or which had a low content of γ'-containing molecules to begin with (i.e., fraction I-2) (Liu, C. Y., et al., supra, 1979; Kaminski, M. and McDonagh, *J., Biochem. J.* 242:881–887, 1987).

Studies of thrombin binding to immobilized fibrin (Fenton, J. W., II, et al., supra, 1988; Berliner, L. J., et al., supra, 1985; Kaminski, M. and McDonagh, J., et al., *J. Biol. Chem.* 258:10530–10535, 1983) or to a modified fibrin clot (des Bβ1-42 fibrin) (Siebenlist, K. R., et al., supra, 1990) could not have distinguished the specific location of any binding site.

We therefore revise the current belief that all non-substrate thrombin binding takes place in the fibrin E domain, to stipulate that only low affinity thrombin binding takes place in this region. We would concur, however, with the notion that thrombin binding in the E domain is likely to represent a residual aspect of the site that participated in fibrinogen substrate recognition. Scatchard analyses indicated a stoichiometry of 1.69 thrombin molecules per fibrin molecule, suggesting that there are two low affinity sites in each dimeric fibrin molecule, corresponding to a fibrinogen substrate recognition site for each pair of fibrinopeptides (FPA, FPB). Whether recognition site binding is the same for FPA and FPB cleavage has yet to be determined.

Unlike the high affinity binding site in the γ' chain, formation of the low affinity site in the E domain is not restricted to a single peptide sequence. Consistent with a previous report (Siebenlist, K. R., et al., supra, 1990), our current data suggest that the β15-42 sequence contributes significantly to non-substrate binding, and that ~60% of low affinity binding is lost by removal of this sequence. Other evidence suggests that the fibrin Aα27-50 sequence contributes as well to low affinity thrombin binding (Vali, Z. and Scheraga, H. A., supra, 1988; Binnie, C. G. and Lord, S. T., supra, 1991). The γ chains in the E domain have also been proposed as contributors to the thrombin binding site (Kaczmarek, E. and McDonagh, J., supra, 1988; Vali, Z. and Scheraga, H. A., supra, 1988), but the evidence for this is not well substantiated.

Fibrinogens New York I (des Bβ9-72) and Naples I (BβA68 T) are dysfibrinogenemias which have been characterized as having impaired thrombin binding (Liu, C. Y., et al., in *Fibrinogen, Fibrin Formation and Fibrinolysis*, Lane, D. A., et al., eds, W. de Gruyter, Berlin, Germany, pp. 79–90, 1986; Koopman, J., et al., *Proc. Natl. Acad. Sci. USA* 89:3478–3482, 1992), presumably related to a defective amino-terminal 'substrate' or 'non-substrate' binding site. A recent study of recombinant γ$_A$-type BβA68 T fibrinogen has reaffirmed the importance of Bβ68 alanine in thrombin-mediated cleavage of Naples I fibrinogen (Lord, S. T., et al., *Biochemistry* 35:2342–2348, 1996). In the case of New York I, which is heterozygotic, thrombin binding to fibrin was 50% of normal, but there was no evidence to suggest a high affinity thrombin binding component (Liu, C. Y., et al., supra, 1986). Similarly, thrombin binding to homozygous Naples I fibrin was reported to be absent (Koopman, J., et al., supra, 1992) and thus there was also no collateral evidence for high affinity thrombin binding to the presumably normal Naples I γ' chain. However, in another report on this same family, thrombin binding to fibrin from a homozygous proband was reduced to only ⅓ of normal (Di Minno, G., et al., *Arterioscl. Thromb.* 11:785–796). The available data derived from studies on Naples I fibrin do not permit an unambiguous distinction to be made as to the presence or absence of a high affinity binding component, although we would have expected only low affinity binding to have been affected.

Direct measurements of thrombin binding to substrate fibrinogen molecules have not been reported owing to the fact that thrombin binding to its substrate is accompanied by concomitant conversion of fibrinogen to fibrin. Instead, estimation of substrate binding affinities have been made from kinetic experiments involving peptide A release from fibrinogen peptides, or fibrinogen itself. The $K_m$ estimated from such studies is 6 to 11 $\mu$M (Martinelli, R. A. and Scheraga, H. A., Biochemistry 19:2343–2350, 1980; Higgins, D. L., et al., J. Biol. Chem. 258:9276–9282, 1983; Hanna, L. S., et al., Biochemistry 23:4681–4687, 1984; Mihalyi, E., Biochemistry 27:976–982, 1988) and the $K_d$ derived from similar kinetic studies was 1.3 to 2.6 $\mu$M (Mathur, A., et al., Biochemistry 32:7568–7573, 1993; Lord, S. T., et al., J. Biol. Chem. 270:24790–24793, 1995). Our results suggest that the high affinity non-substrate site has a significantly higher affinity for thrombin exosite binding ($K_d$, 0.26 $\mu$M) than that estimated from the $K_m$ or the $K_d$ derived for the substrate site (Martinelli, R. A. and Scheraga, H. A., supra, 1980; Higgins, D. L., et al., supra, 1983; Hanna, L. S., et al., supra, 1984; Mihalyi, E., supra, 1988; Mathur, A., et al., supra, 1993; Lord, S. T., et al., supra, 1995). Nevertheless, the γ' site itself in fibrinogen is not an effective competitor for thrombin binding and cleavage at the fibrinogen substrate site, as assessed by our thrombin time measurements in this study and in another (Mosesson, M. W. and Finlayson, J. S., supra, 1963). It therefore seems likely that the substrate binding site itself will prove to have a higher binding affinity for thrombin than has previously been estimated from $K_m$ measurements, by analogy with hirudin, which has a higher binding affinity for thrombin as a bivalent molecule than does its C-terminal exosite binding sequence alone.

The physiological role that the γ' sequence plays in modulating thrombin function still remains to be determined. It is very likely that the measurable thrombin clotting activity found in fibrin and fibrin degradation products (Francis, W. C., et al., J. Lab. Clin. Med. 102:220–230, 1983; Weitz, J. I., et al., J. Clin. Invest. 86:385–391, 1990; Kumar, R., et al., Thromb. Haemost. 72:713–721, 1994; Kumar, R., et al., Thromb. Haemost. 74:962–968, 1995) is attributable to non-substrate binding at the γ' site, or the low affinity site, or at both sites. In light of our present findings, it will be important to study the relationship between thrombin binding to γ'-containing fibrin, and thrombin activation of coagulation factors such as factors V, VIII or XIII, or cellular receptors such as those on platelets and endothelial cells.

Example 2

Determination of the γ' Sequences which are Essential for Binding to the Thrombin Exosite 1. In General We used synthetic peptides to determine which amino acid residues of the γ' chain account for high affinity thrombin binding.

2. Materials and Methods

Peptide synthesis

Peptides were synthesized on a 9050 Pepsynthesizer (Millipore, Bedford, Mass.) according to manufacturer-specified protocols (FastPep, 0.1 mMol scale) using standard FMOC chemistry. The peptides were purified by reverse phase HPLC (Beckman Instruments, San Ramon, Calif.) to >90% purity using a C18 column and their structure verified when appropriate by electrospray mass spectrometry (EMS).

Sulfation of tyrosine

Tyrosine residues of some peptides were sulfated essentially as described by Maraganore, et al. (Marganore, J., et al., J. Biol. Chem. 264:8692–8698, 1989) except that the concentration of N,N,-dicyclohexylcarbodiimide (DCC) was 1000 fold higher than reported, in agreement with the reagent concentration reported by Nakahara, et al. (Nakahara, T., et al., Anal. Biochem. 154:194–199, 1986). Briefly, 5 mg dried peptide was dissolved in 50 $\mu$l of dimethylformamide (DMF) (stored over alumina-silicate molecular sieves) and freeze-dried in a Speedvac apparatus to remove residual water. The pellet was then dissolved in 120 $\mu$l of DMF containing 1.0 N $H_2SO_4$. Sulfation was initiated by addition of 30 $\mu$l of DCC (1.25 mg/pl of DMF) for 5–10 minutes at room temperature. The reaction was terminated by addition of 1.0 ml 100 mM ammonium bicarbonate. Following a 5 minute incubation at room temperature, the precipitate that had formed after DCC addition was removed by centrifugation (12,000×g for 5 minutes) and the supernatant solution dialyzed in a 1000 molecular weight cutoff tubing (Spectrum) against 100 mM ammonium bicarbonate solution. Sulfation was determined by the shift in the absorbance maximum from 280 nm to 260.5 nm, and verified by EMS.

Inhibition studies

To determine the capacity of the peptides to inhibit thrombin binding, a 200 $\mu$l clot containing fibrin (0.5 nmoles) and $^{125}$I-PPACK-thrombin (0.1 nmoles) in 0.05M HEPES, 0.10M NaCl buffer, pH 7.4, and 0.01% (w/v) polyethylene glycol 8000 was formed in the presence of varying concentrations of peptide. The amount of thrombin bound to the clot was determined by counting the $^{125}$I radioactivity in a gamma counter. The $IC_{50}$ was estimated as the concentration of peptide which reduced the amount of thrombin bound by 50%. For most studies, peak 1 fibrin was used to assess the inhibitory capacity of the peptides. Similar qualitative thrombin-binding results were obtained using peak 2 fibrin (FIG. 6), but higher levels of peptide were needed to inhibit binding since this molecule contains the high affinity thrombin-binding site.

Figure 6:
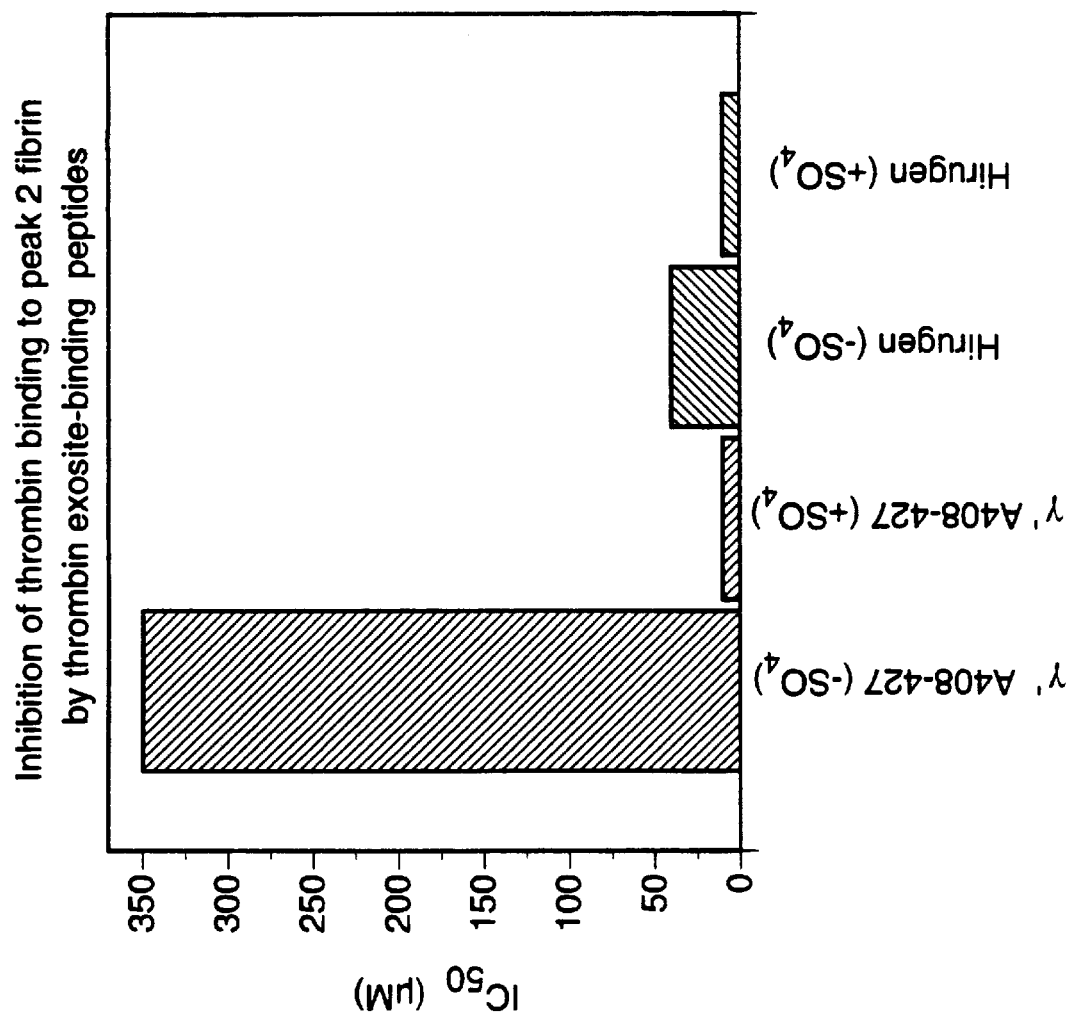
FIG. 6 is a bar graph showing inhibition of thrombin binding to peak 2 fibrin by various peptides containing native sequences.
Figure 7:
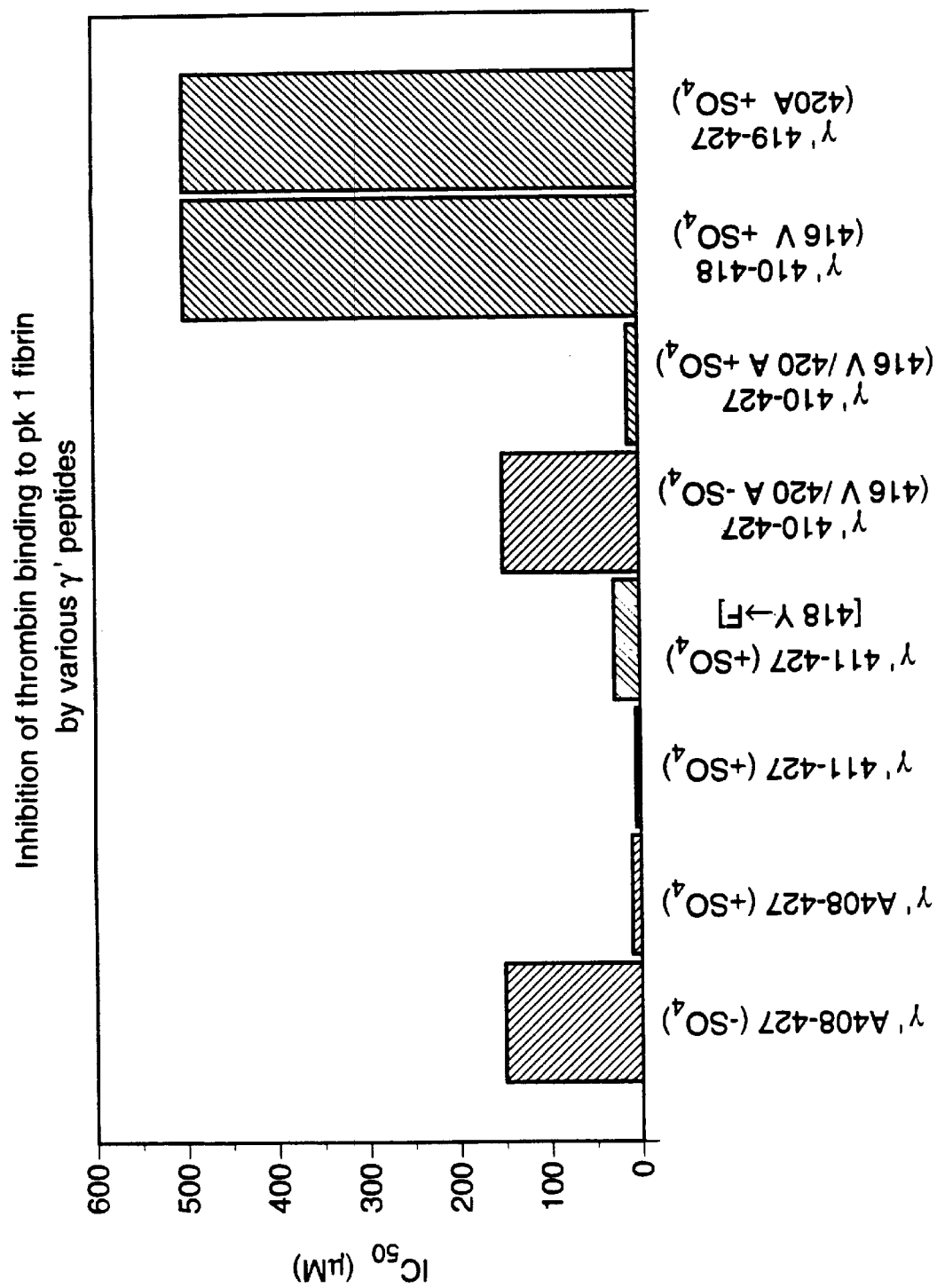
FIG. 7 is a bar graph showing inhibition of thrombin binding to peak 1 fibrin by various peptides containing the native γ' sequence or with Val for Thr and Ala for Ser substitutions.

Previous studies have shown that sulfation of the tyrosine residue in the hirudin 53-64 peptide (hirugen) increased the affinity of the peptide for the thrombin exosite (Maraganore, J., et al., supra, 1989). Our initial studies were done with the native human sequence γ' A408–427 either with or without sulfation (FIG. 6). We found that the γ' A408–427 sequence had a greater inhibitory effect on thrombin binding to peak 2 fibrin following tyrosine sulfation, with an $IC_{50}$ comparable to that of sulfated hirugen (14 $\mu$M versus 10 $\mu$M, respectively). Even greater inhibitory effects were seen with a tyrosine-sulfated peptide (γ' 411–427) in a peak 1 fibrin system (FIG. 7). When the tyrosine at 418 in this sequence was substituted with phenylalanine (γ' 411–427/418F) and sulfated, there was an increase in $IC_{50}$ compared with the doubly tyrosine-sulfated peptide, but the mono-sulfated peptide (411–427/418F) still had a lower $IC_{50}$ than non-sulfated γ' A408–427 (FIG. 7). EMS indicated that there had been also sulfation at γ' residues other than at tyrosine, presumably the hydroxylated moieties at threonine 416, or at serine 420, or both.

In order to continue our studies with tyrosine-sulfated peptides we circumvented sulfation of the threonine and serine residues by substituting valine for threonine at 416 and alanine for serine at 420 (Table 4). The $IC_{50}$ determined for sulfated γ' 410–427 (416V/420A) and the sulfated native γ' A408–427 or γ' 411–472 sequences were similar (FIG. 7). As seen with the native sequences, sulfation of γ' 410–427 (416V/420A) significantly decreased the $IC_{50}$. Comparing the native sequence to the val and ala substituted peptides indicated no significant change in $IC_{50}$ as a result of the substitutions for threonine and serine. Although both were sulfated, neither the amino-terminal γ' 410–418(416V) nor the carboxy-terminal γ' 419–427(420A) segment of this peptide had any significant inhibition of thrombin binding (FIG. 7).

Figure 8:
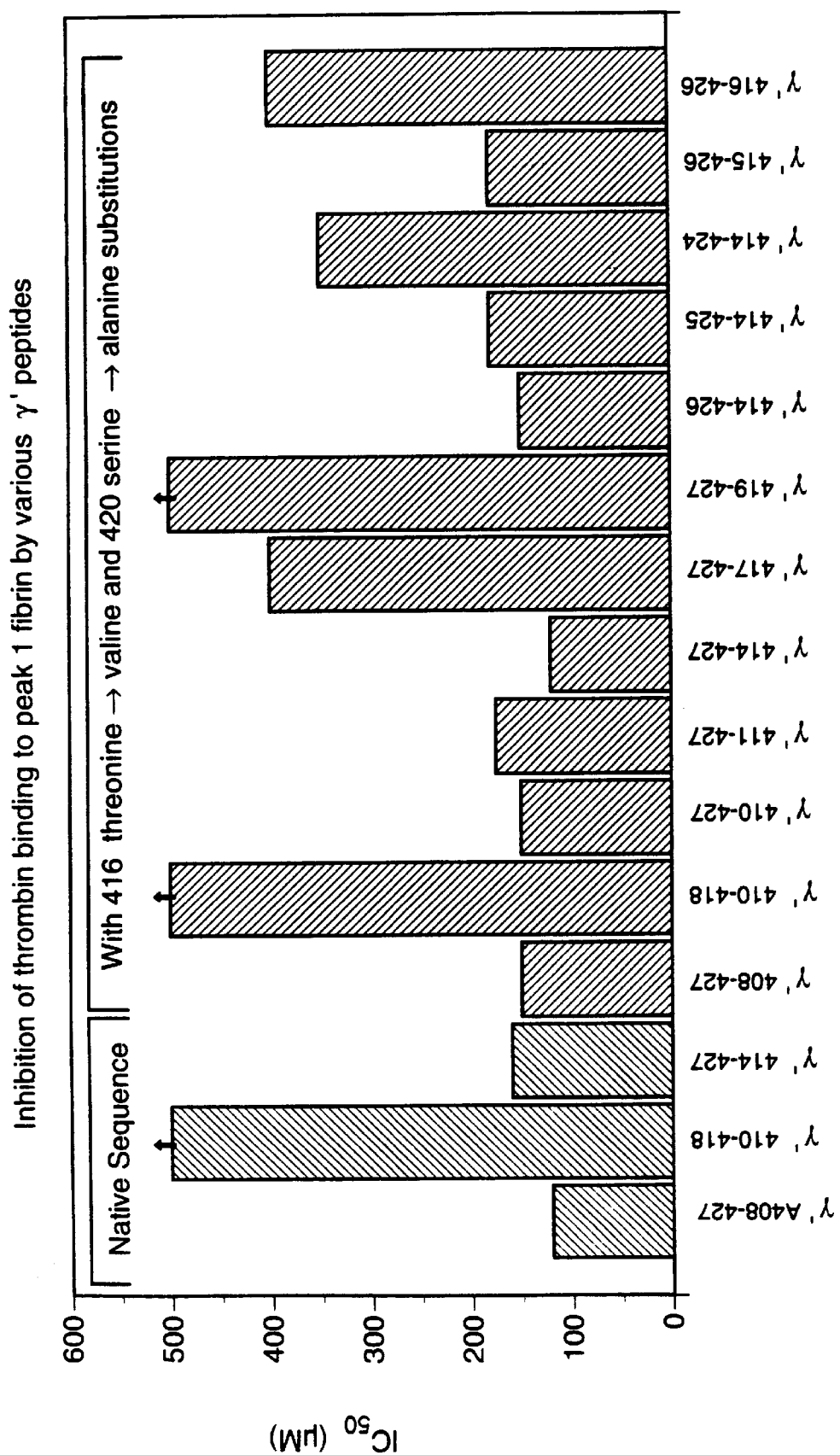
FIG. 8 is a bar graph indicating inhibition of thrombin binding to peak 1 fibrin by various γ' peptides.

To narrow the essential sequences necessary for thrombin binding, subsequent inhibition studies were done with a series of non-sulfated γ' peptides containing the 416 T→V and 420 S→A substitutions (FIG. 8). Peptides γ' 408–427, γ' 410–427, γ' 411–427, γ' 414–427, showed no significant increases in IC$_{50}$. The γ' 414–427 peptide had the lowest IC$_{50}$. Removal of carboxy-terminal 427 or 426 resulted in a small increase in IC$_{50}$, whereas removal of residues beyond 414 resulted in a significant increase in IC$_{50}$. These findings indicate that the γ' 414–427 sequence is optimal for thrombin exosite binding.

TABLE 4

| | | | | | | | | | | | | | | | | | | | | |
|---|---|---|---|---|---|---|---|---|---|---|---|---|---|---|---|---|---|---|---|---|
| γ' A408–427 | A | V | R | P | E | H | P | A | E | T | E | Y | E | S | L | Y | P | E | D | D | L |
| γ' 410–418 | | | | P | E | H | P | A | E | T | E | Y | | | | | | | | | |
| γ' 411–427 | | | | | E | H | P | A | E | T | E | Y | E | S | L | Y | P | E | D | D | L |
| γ' 411–427 (418F) | | | | | E | H | P | A | E | T | E | F | E | S | L | Y | P | E | D | D | L |
| γ' 414–427 | | | | | | | | A | E | T | E | Y | E | S | L | Y | P | E | D | D | L |
| γ' 408–427 (416V/420A) | | V | R | P | E | H | P | A | E | V | E | Y | E | A | L | Y | P | E | D | D | L |
| γ' 410–418 (416V) | | | | P | E | H | P | A | E | V | E | Y | | | | | | | | | |
| γ' 411–417 (416V/420A) | | | | | E | H | P | A | E | V | E | Y | E | A | L | Y | P | E | D | D | L |
| γ' 414–427 (416V/420A) | | | | | | | | A | E | V | E | Y | E | A | L | Y | P | E | D | D | L |
| γ' 417–427 (420A) | | | | | | | | | | | E | Y | E | A | L | Y | P | E | D | D | L |
| γ' 419–427 (420A) | | | | | | | | | | | | | E | A | L | Y | P | E | D | D | L |
| γ' 414–426 (416V/420A) | | | | | | | | A | E | V | E | Y | E | A | L | Y | P | E | D | D | |
| γ' 414–425 (416V/420A) | | | | | | | | A | E | V | E | Y | E | A | L | Y | P | E | D | | |
| γ' 414–424 (416V/420A) | | | | | | | | A | E | V | E | Y | E | A | L | Y | P | E | | | |
| γ' 415–426 (416V/420A | | | | | | | | | E | V | E | Y | E | A | L | Y | P | E | D | D | |
| γ' 416–426 (416V/420A) | | | | | | | | | | V | E | Y | E | A | L | Y | P | E | D | D | |
| Hirugen (Hir 53–64) | N | G | D | F | E | E | I | P | E | E | Y | L | | | | | | | | | |

We claim:

1. A thrombin inhibitor comprising (a) a means for inactivating or sequestering thrombin, and (b) a portion of the fibrinogen γ' chain that binds at the anion-binding exosite of thrombin, wherein the portion of the fibrinogen γ' chain consists of residues 414–425 of the native fibrinogen γ' sequence or its pharmaceutically acceptable salts.

2. A thrombin inhibitor comprising (a) a means for inactivating or sequestering thrombin, and (b) a portion of the fibrinogen γ' chain that binds at the anion-binding exosite of thrombin, wherein the portion of the fibrinogen γ' chain consists of residues 414–427 of the native fibrinogen γ' sequence or its pharmaceutically acceptable salts.

* * * * *

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
      (A) LENGTH: 4 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Ala Gly Asp Val
1

(2) INFORMATION FOR SEQ ID NO:2:

(i) SEQUENCE CHARACTERISTICS:
      (A) LENGTH: 20 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

Val Arg Pro Glu His Pro Ala Glu Thr Glu Tyr Glu Ser Leu Tyr Pro
1             5                  10                 15

Glu Asp Asp Leu
        20

(2) INFORMATION FOR SEQ ID NO:3:

(i) SEQUENCE CHARACTERISTICS:
      (A) LENGTH: 12 amino acids (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:3:

Val Ser Val Glu His Glu Val Asp Val Glu Tyr Pro
1               5                  10

(2) INFORMATION FOR SEQ ID NO:4:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:4:

Val Arg Val Glu His His Val Glu Ile Glu Tyr Asp
1               5                  10

(2) INFORMATION FOR SEQ ID NO:5:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:5:

Asn Gly Asp Phe Glu Glu Ile Pro Glu Glu Tyr Leu Gln
1               5                  10

(2) INFORMATION FOR SEQ ID NO:6:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:6:

Phe Pro Arg Phe Pro Arg Pro
1               5

(2) INFORMATION FOR SEQ ID NO:7:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:7:

Gln Ser His Asn Asp Gly
1               5

(2) INFORMATION FOR SEQ ID NO:8:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..14
        (D) OTHER INFORMATION: /note= "where X1 is a nonpolar
            amino acid; X2 is an anionic amino acid; X3 is a
            polar or nonpolar amino acid; X4 is an anionic amino
            acid; X5 is Tyr; X6 is an anionic amino acid; X7 is a
            polar or nonpolar amino acid; X8 is a nonpolar amino
            acid; X9 is Tyr; X10 is Pro, X11 is an anionic amino
            acid; X12 is an anionic amino acid; X13 is an anionic
            amino acid; and X14 is a nonpolar amino acid.

(xi) SEQUENCE DESCRIPTION: SEQ ID NO:8:

Xaa Xaa Xaa Xaa Xaa Xaa Xaa Xaa Xaa Xaa Xaa Xaa Xaa Xaa
1           5                  10

(2) INFORMATION FOR SEQ ID NO:9:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Ala Val Arg Pro Glu His Pro Ala Glu Thr Glu Tyr Glu Ser Leu Tyr
1           5                  10               15

Pro Glu Asp Asp Leu
        20

(2) INFORMATION FOR SEQ ID NO:10:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Pro Glu His Pro Ala Glu Thr Glu Tyr
1           5

(2) INFORMATION FOR SEQ ID NO:11:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Glu His Pro Ala Glu Thr Glu Tyr Glu Ser Leu Tyr Pro Glu Asp Asp
1           5                  10               15

Leu (2) INFORMATION FOR SEQ ID NO:12:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Glu His Pro Ala Glu Thr Glu Phe Glu Ser Leu Tyr Pro Glu Asp Asp
1               5                   10                  15

Leu
```

(2) INFORMATION FOR SEQ ID NO:13:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Ala Glu Thr Glu Tyr Glu Ser Leu Tyr Pro Glu Asp Asp Leu
1               5                   10
```

(2) INFORMATION FOR SEQ ID NO:14:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Val Arg Pro Glu His Pro Ala Glu Val Glu Tyr Glu Ala Leu Tyr Pro
1               5                   10                  15

Glu Asp Asp Leu
            20
```

(2) INFORMATION FOR SEQ ID NO:15:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Pro Glu His Pro Ala Glu Val Glu Tyr
1               5
```

(2) INFORMATION FOR SEQ ID NO:16:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Glu His Pro Ala Glu Val Glu Tyr Glu Ala Leu Tyr Pro Glu Asp Asp
1               5                  10                  15

Leu (2) INFORMATION FOR SEQ ID NO:17:

(i) SEQUENCE CHARACTERISTICS:
         (A) LENGTH: 14 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:17:

Ala Glu Val Glu Tyr Glu Ala Leu Tyr Pro Glu Asp Asp Leu
1               5                  10

(2) INFORMATION FOR SEQ ID NO:18:

(i) SEQUENCE CHARACTERISTICS:
         (A) LENGTH: 11 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:18:

Glu Tyr Glu Ala Leu Tyr Pro Glu Asp Asp Leu
1               5                  10

(2) INFORMATION FOR SEQ ID NO:19:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:19:

Glu Ala Leu Tyr Pro Glu Asp Asp Leu
1               5

(2) INFORMATION FOR SEQ ID NO:20:

(i) SEQUENCE CHARACTERISTICS:
         (A) LENGTH: 13 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:20:

Ala Glu Val Glu Tyr Glu Ala Leu Tyr Pro Glu Asp Asp
1               5                  10

(2) INFORMATION FOR SEQ ID NO:21:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

```
Ala Glu Val Glu Tyr Glu Ala Leu Tyr Pro Glu Asp
1               5                   10
```

(2) INFORMATION FOR SEQ ID NO:22:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

```
Ala Glu Val Glu Tyr Glu Ala Leu Tyr Pro Glu
1               5                   10
```

(2) INFORMATION FOR SEQ ID NO:23:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
Glu Val Glu Tyr Glu Ala Leu Tyr Pro Glu Asp Asp
1               5                   10
```

(2) INFORMATION FOR SEQ ID NO:24:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

```
Val Glu Tyr Glu Ala Leu Tyr Pro Glu Asp Asp
1               5                   10
```

(2) INFORMATION FOR SEQ ID NO:25:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

```
Asn Gly Asp Phe Glu Glu Ile Pro Glu Glu Tyr Leu
1               5                   10
```